US008728076B2

(12) United States Patent
Livneh

(10) Patent No.: US 8,728,076 B2
(45) Date of Patent: May 20, 2014

(54) SURGICAL APPARATUS WITH REMOVABLE TOOL CARTRIDGE

(75) Inventor: Steve Livneh, Amherstburg (CA)

(73) Assignee: Bovie Medical Corporation, Clearwater, FL (US)

( * ) Notice: Subject to any disclaimer, the term of this patent is extended or adjusted under 35 U.S.C. 154(b) by 1198 days.

(21) Appl. No.: 12/338,431

(22) Filed: Dec. 18, 2008

(65) Prior Publication Data

US 2009/0157074 A1 Jun. 18, 2009

Related U.S. Application Data

(60) Provisional application No. 61/014,612, filed on Dec. 18, 2007, provisional application No. 61/117,380, filed on Nov. 24, 2008, provisional application No. 61/119,150, filed on Dec. 2, 2008.

(51) Int. Cl.
*A61M 31/00* (2006.01)
(52) U.S. Cl.
USPC ............. 606/48; 606/29; 606/41; 606/46; 606/51; 227/175.1; 29/407.04
(58) Field of Classification Search
USPC ............. 606/29, 41, 46, 48, 51; 227/175.1
See application file for complete search history.

(56) References Cited

U.S. PATENT DOCUMENTS

| | | | | |
|---|---|---|---|---|
| 3,496,500 A | * | 2/1970 | Romary | 335/205 |
| 5,531,744 A | * | 7/1996 | Nardella et al. | 606/48 |
| 5,564,615 A | * | 10/1996 | Bishop et al. | 227/175.1 |
| 5,582,611 A | * | 12/1996 | Tsuruta et al. | 606/46 |
| 5,601,224 A | * | 2/1997 | Bishop et al. | 227/175.1 |
| 5,830,231 A | | 11/1998 | Geiges, Jr. | |
| 7,585,295 B2 | * | 9/2009 | Ben-Nun | 606/28 |
| 7,766,910 B2 | * | 8/2010 | Hixson et al. | 606/51 |
| 7,951,150 B2 | * | 5/2011 | Johnson et al. | 606/51 |
| 2003/0018331 A1 | * | 1/2003 | Dycus et al. | 606/48 |
| 2003/0069571 A1 | * | 4/2003 | Treat et al. | 606/29 |
| 2004/0220602 A1 | * | 11/2004 | Deng et al. | 606/170 |

(Continued)

FOREIGN PATENT DOCUMENTS

| | | |
|---|---|---|
| EP | 0908150 A1 | 4/1999 |
| EP | 1810625 A1 | 7/2007 |

(Continued)

OTHER PUBLICATIONS

International Search Report and Written Opinion of the International Searching Authority for PCT/US2008/013931 mailed Jul. 3, 2009.

*Primary Examiner* — Jason Flick
*Assistant Examiner* — Scott Medway
(74) *Attorney, Agent, or Firm* — Michael J. Porco; Gerald E. Hespos; Matthew T. Hespos

(57) ABSTRACT

A surgical apparatus for coagulating and cutting tissue includes a handle assembly and a tool cartridge. The tool cartridge includes electrically conductive movable tools, such as jaws and a blade, for cutting tissue. The jaws and blade each are connected to a transmission to facilitate movement. Multiple sheaths are used to encompass and protect the transmissions. Slidable grips are disposed outside of the sheaths and operatively connected to the transmissions that are disposed within the sheaths. At least one lever is supported by the handle assembly and engagable with the grips to facilitate movement of the grips, and thus, the tools.

17 Claims, 19 Drawing Sheets

(56) References Cited

U.S. PATENT DOCUMENTS

| | | | |
|---|---|---|---|
| 2005/0033278 A1* | 2/2005 | McClurken et al. | 606/41 |
| 2006/0116675 A1* | 6/2006 | McClurken et al. | 606/51 |
| 2007/0055231 A1* | 3/2007 | Dycus et al. | 606/51 |
| 2007/0062017 A1* | 3/2007 | Dycus et al. | 29/407.04 |
| 2007/0179499 A1 | 8/2007 | Garrison | |
| 2012/0118078 A1* | 5/2012 | Chen | 73/862.21 |

FOREIGN PATENT DOCUMENTS

| | | | | |
|---|---|---|---|---|
| EP | 1810625 B1 * | 7/2007 | | A61B 18/14 |
| JP | 56102442 A * | 8/1981 | | B23Q 1/08 |
| WO | 2009082477 A2 | 7/2009 | | |
| WO | 2009082477 A4 | 11/2009 | | |

* cited by examiner

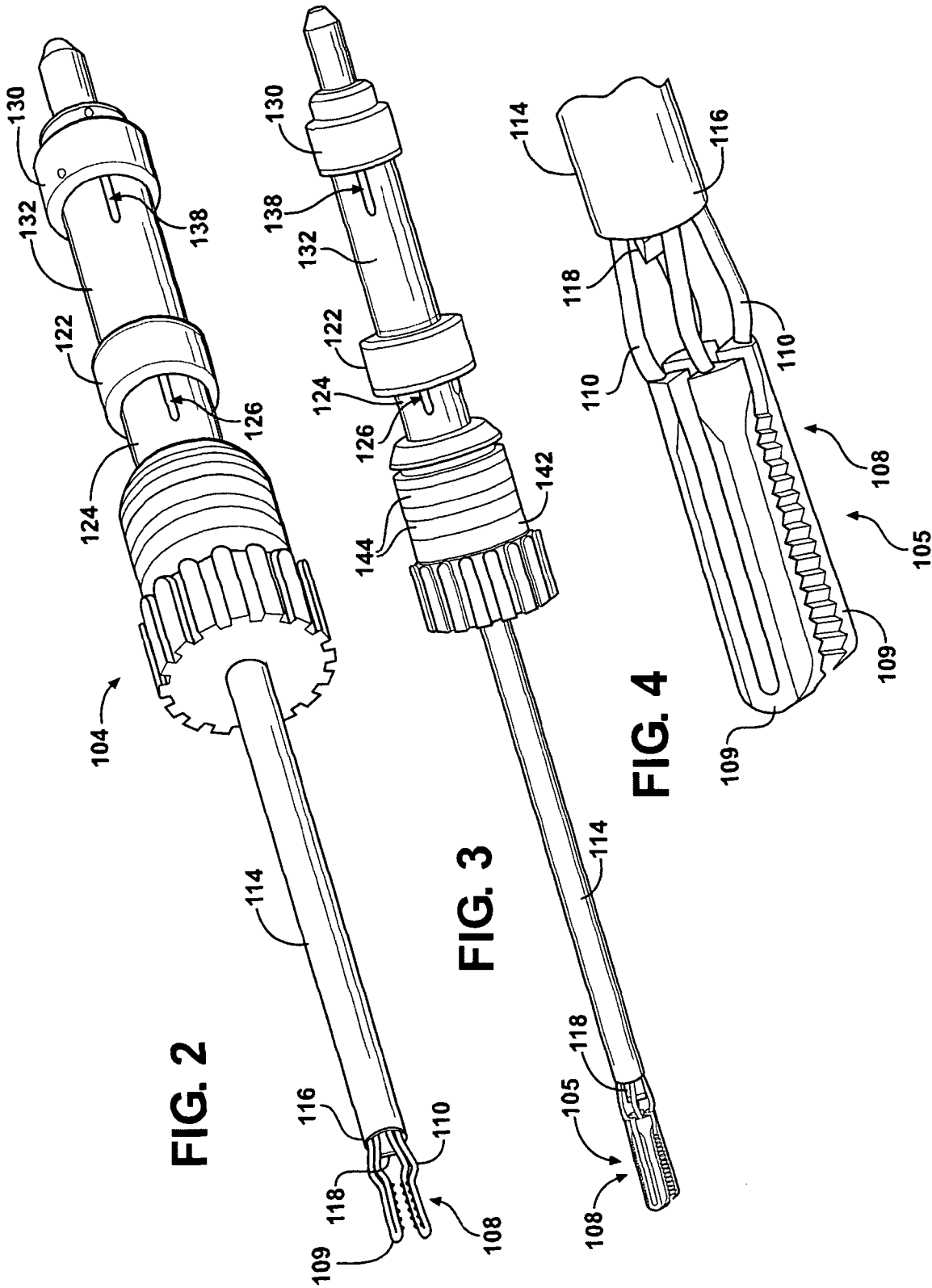

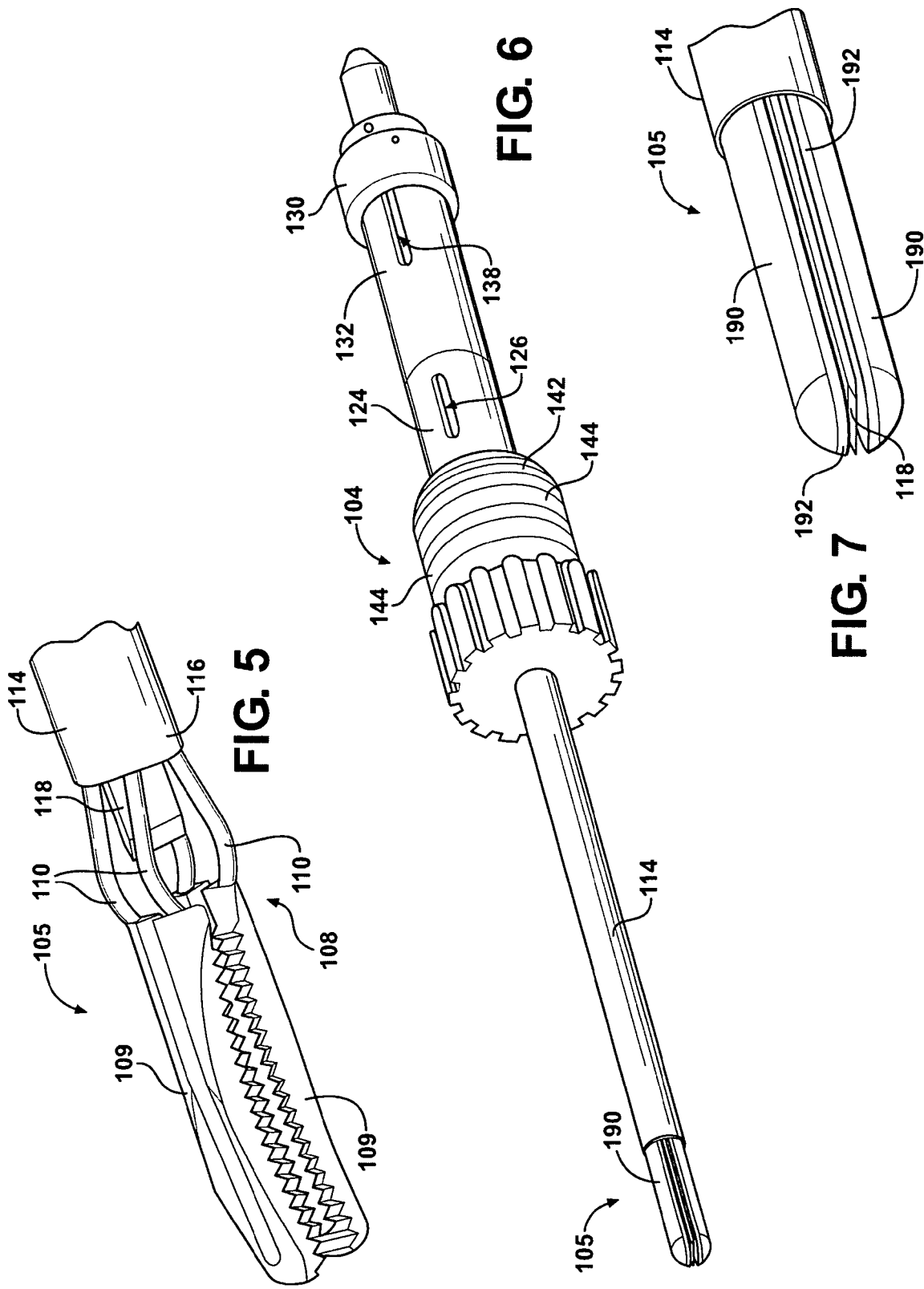

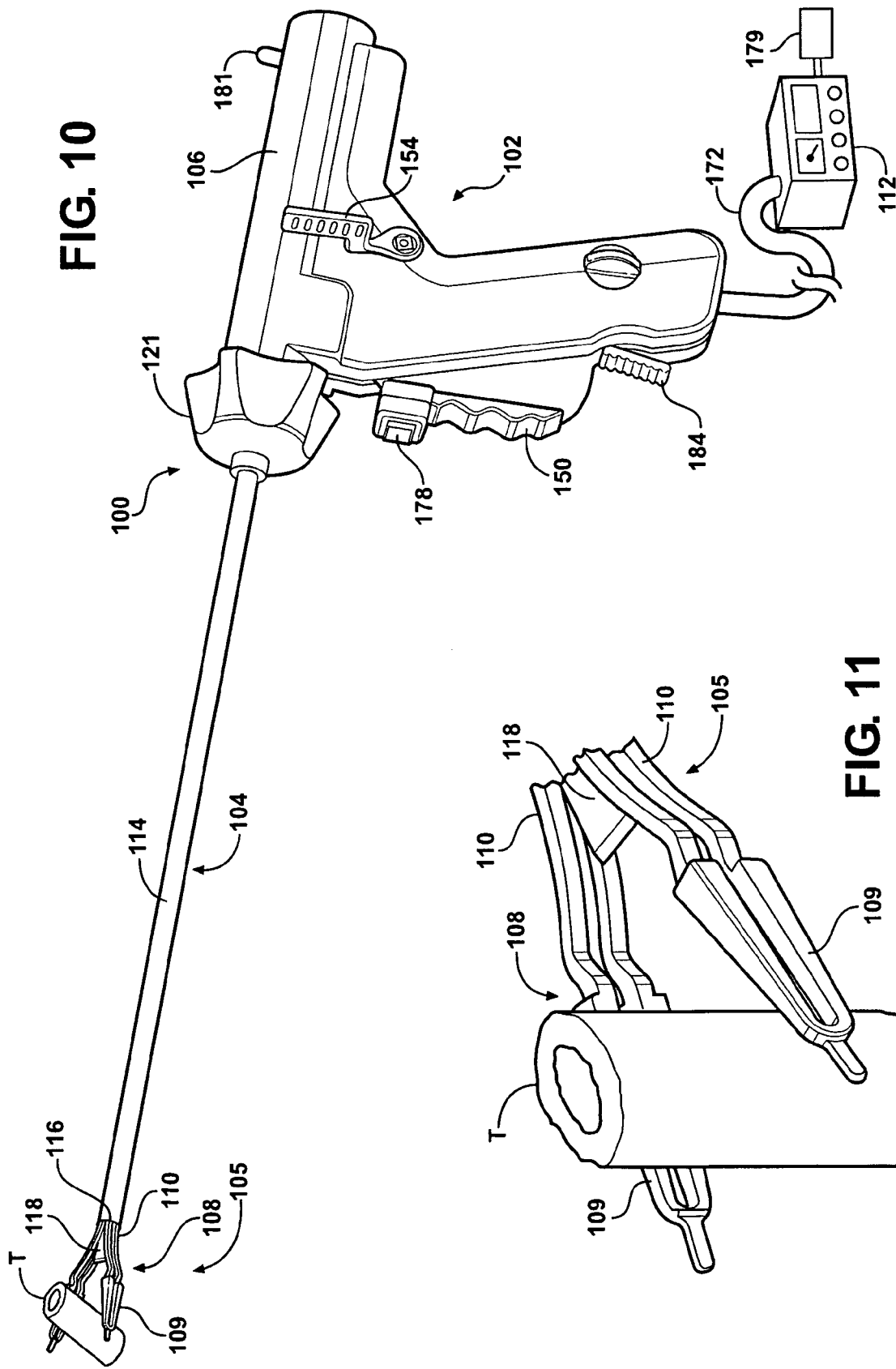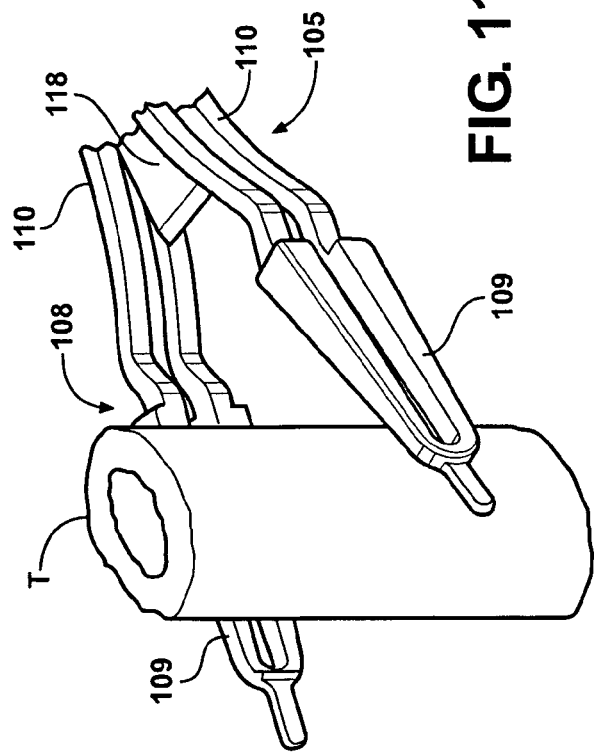

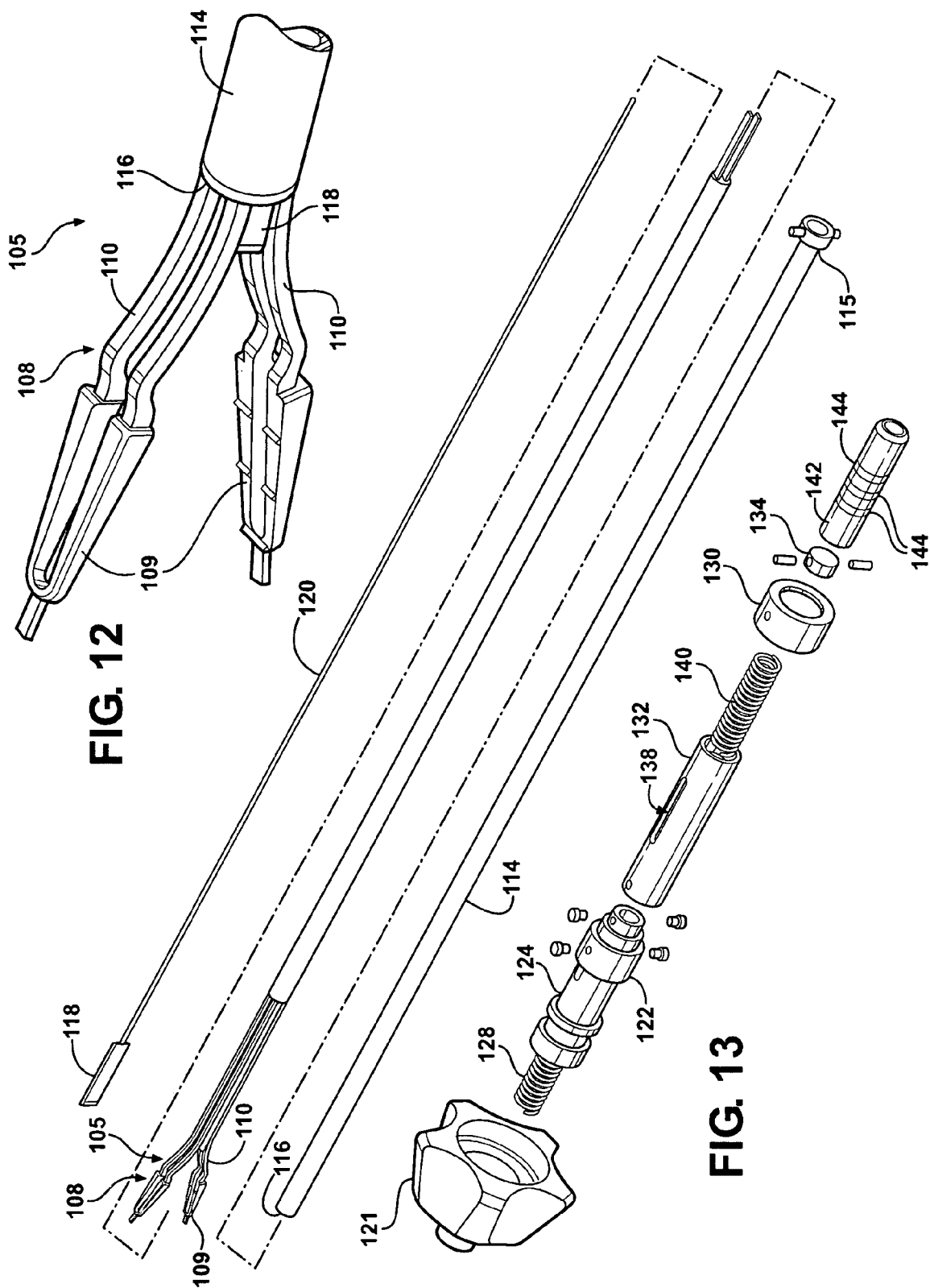

SURGICAL APPARATUS WITH REMOVABLE TOOL CARTRIDGE

CROSS REFERENCE TO RELATED APPLICATION

This application claims the benefit of provisional patent application No. 61/014,612, filed Dec. 18, 2007, provisional patent application No. 61/117,380, filed Nov. 24, 2008, and provisional patent application No. 61/119,150, filed Dec. 2, 2008, which are each hereby incorporated by reference.

BACKGROUND OF THE INVENTION

1. Field of the Invention

The subject invention relates to surgical instruments. Specifically, the subject invention relates to electrosurgical instruments for cutting tissue such as blood vessels.

2. Description of the Related Art

Electrosurgical instruments have gained high acceptance in the medical community for coagulating and cutting tissue, such as blood vessels. These instruments are typically "one-piece" assemblies where the delicate tools used in the surgery are permanently affixed to handle and trigger mechanisms.

Because of this one-piece construction, these instruments tend to be expensive. Furthermore, due to the risk of infections, these instruments need to be sterilized and replaced often. Obviously, routinely replacing these expensive instruments drives up the cost of surgical procedures which must ultimately be borne by the patient.

Therefore, there is an opportunity to provide a surgical instrument that has more performance in a cost effective, disposable device.

SUMMARY OF THE INVENTION AND ADVANTAGES

A first aspect of the invention provides a surgical apparatus for coagulating and cutting tissue. The apparatus includes a handle assembly having a housing and a tool cartridge at least partially receivable in the housing. The tool cartridge includes a tool for use in coagulating and cutting tissue and a transmission operatively connected to the tool and longitudinally movable between positions. The tool cartridge also includes a sheath enclosing at least part of the transmission and defining at least one slot. A grip is disposed outside of the sheath and operatively connected to the transmission through the at least one slot. The handle assembly also includes a tool actuation lever operatively engagable with the grip of the tool cartridge such that the grip and the transmission move to actuate the tool in relation to actuation of the tool actuation lever.

A second aspect of the invention provides a surgical apparatus for coagulating and cutting tissue. The apparatus includes a tool cartridge having a tool for use in cutting tissue. A handle assembly includes a housing for supporting the tool cartridge. The housing defines an opening for accommodating the tool cartridge such that part of the tool cartridge is disposed inside the housing and part of the tool cartridge is disposed outside the housing. The apparatus also includes a gate mechanism for shuttering the opening when the tool cartridge is absent from the handle assembly.

A third aspect of the invention provides A surgical apparatus for coagulating and cutting tissue of a body. The apparatus includes a handle assembly having a first lever and a second lever. A tool cartridge is supported by the handle assembly. The tool cartridge includes a pair of jaws electrically connected to a power source and movable in conjunction with the first lever for grasping the tissue. The tool cartridge also includes a blade electrically connected to the power source and movable in conjunction with the second lever between positions. A cut-coag switch is operatively connected to the second lever for automatically switching between a coagulation mode and a cutting mode as the blade is moved between positions.

The surgical apparatus of the subject invention provides numerous advantages over the prior art. The use of sheaths enclosing the transmission helps protect these components from dirt or damage, allowing positioning of springs and pistons thus executing desired movements. Likewise, the gate mechanism also protects the interior of the handle assembly from debris and damage. Moreover, the apparatus allows for automatic switching between coagulation and cutting modes. This automatic switching allows the surgeon to concentrate on the surgical procedure, instead of worrying about turning dials on a power supply.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 2 is a perspective view of a first design of the tool cartridge for use with the handle assembly of the first embodiment;

FIG. 3 is a perspective view of a second design of the tool cartridge for use with the handle assembly of the first embodiment;

FIG. 4 is a close-up perspective view of a pair of jaws and a blade of the tool cartridge of the second design;

FIG. 5 is a close-up perspective view of the jaws and a blade of a third design of the tool cartridge;

FIG. 6 is a perspective view of a fourth design of the tool cartridge for use with the handle assembly of the first embodiment;

FIG. 7 is a close-up perspective view of a pair of electrodes and the blade of the tool cartridge of the fourth design;

FIG. 10 is a perspective view of a second embodiment of the surgical apparatus showing the tool cartridge installed in the handle assembly with the jaws grasping tissue T;

FIG. 11 is a close-up perspective view of the pair of jaws and the blade of the second embodiment grasping tissue T;

FIG. 12 is a close-up perspective view of the pair of jaws of the second embodiment FIG. 13 is an exploded view of the tool cartridge of the second embodiment;

DETAILED DESCRIPTION OF THE INVENTION

Referring to the Figures, wherein like numerals indicate like parts throughout the several views, a surgical apparatus for cutting tissue is shown at 100.

Figure 1:
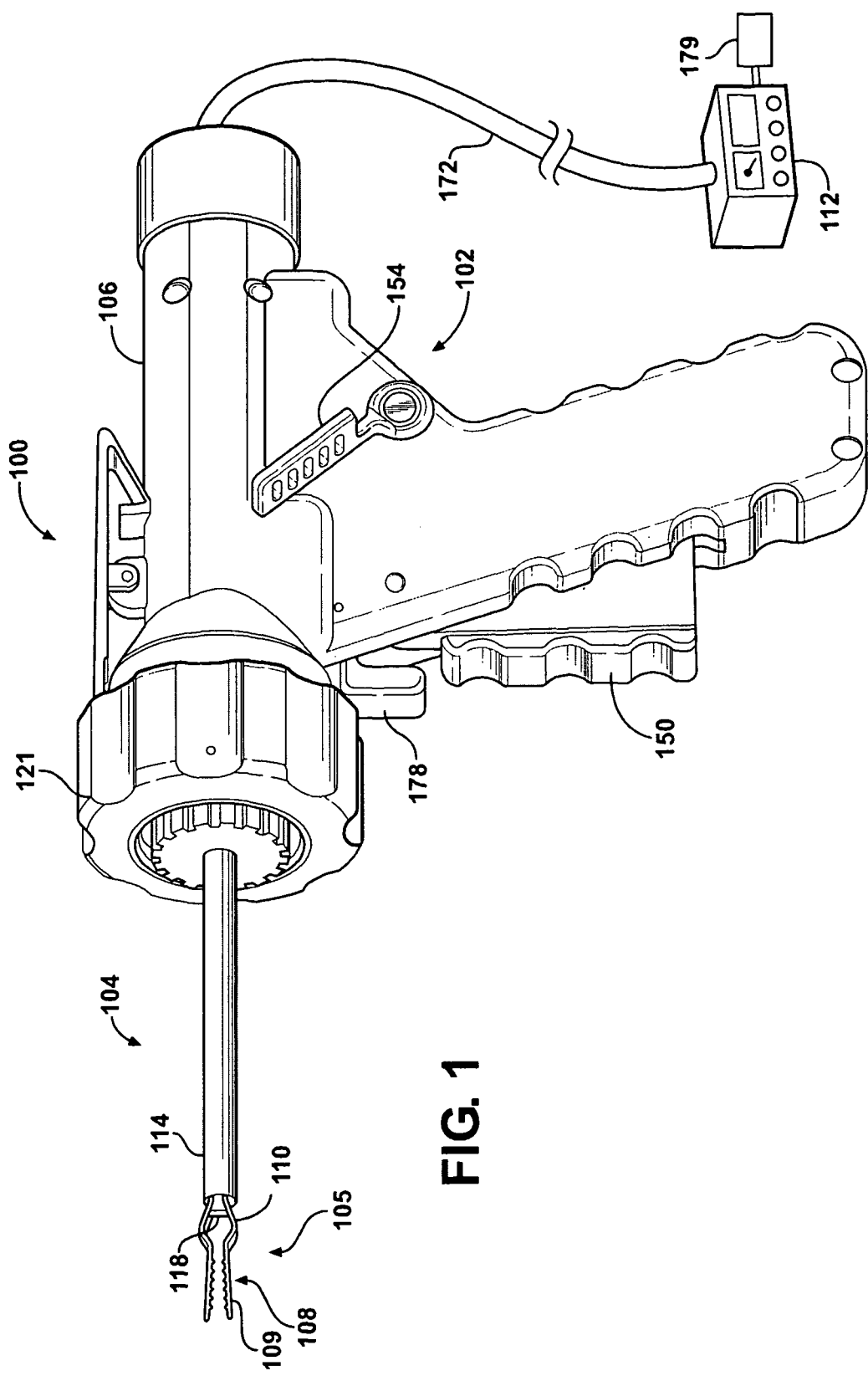
FIG. 1 is a perspective view of a first embodiment of a surgical apparatus showing a tool cartridge installed in a handle assembly.
Figure 9:
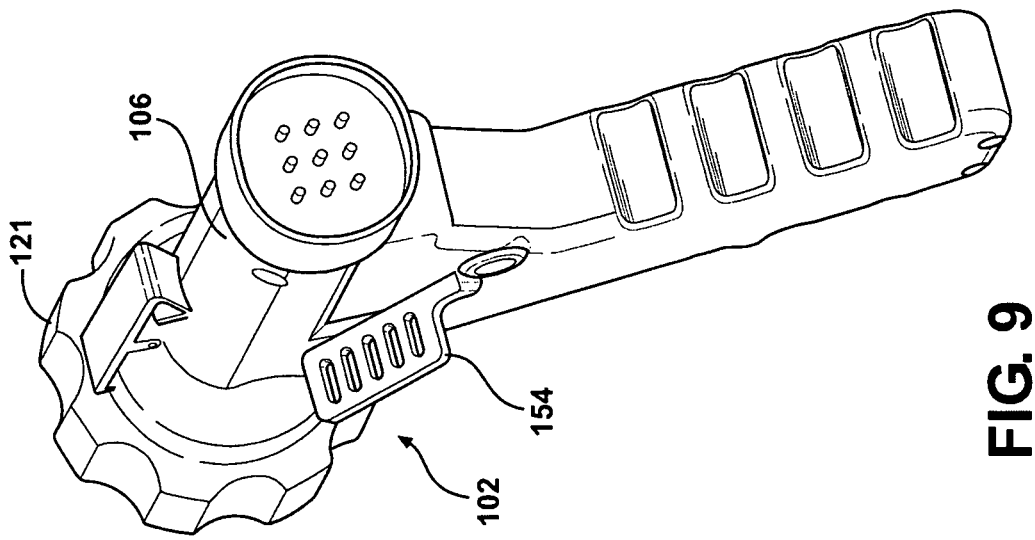
FIG. 9 is a perspective view of the handle assembly of the first embodiment showing electrical connecting pins for connecting the handle assembly to an electrosurgical power source.
Figure 8:
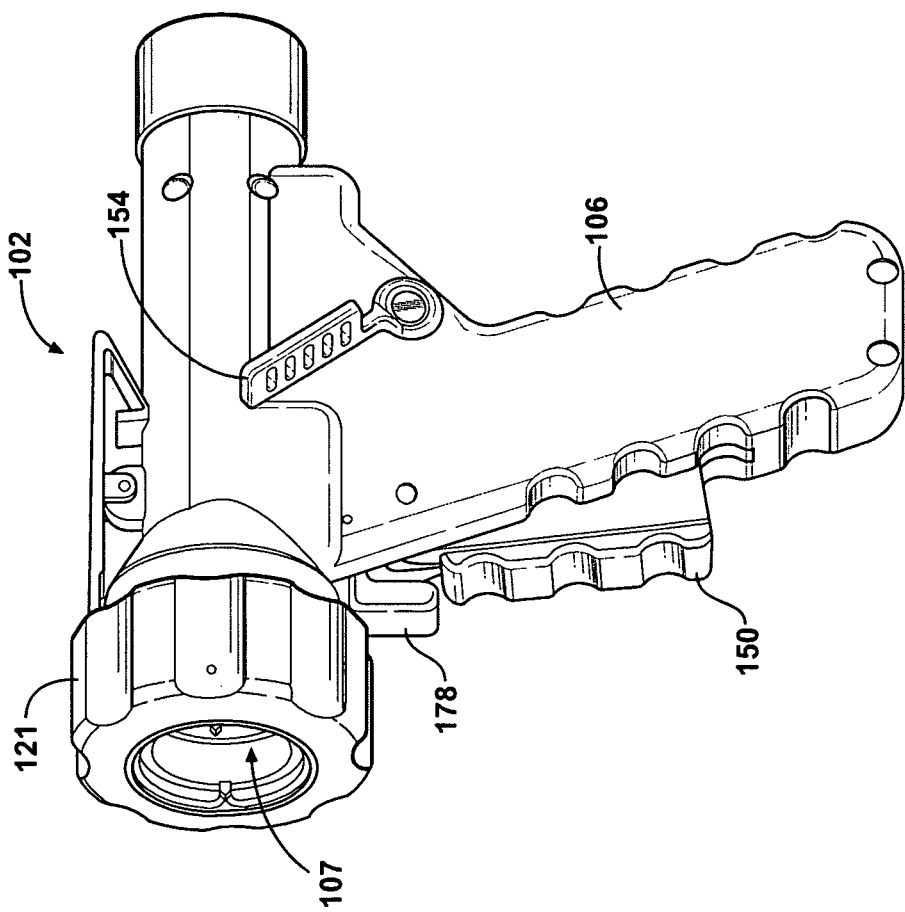
FIG. 8 is a perspective view of the handle assembly of the first embodiment.
Figure 14:
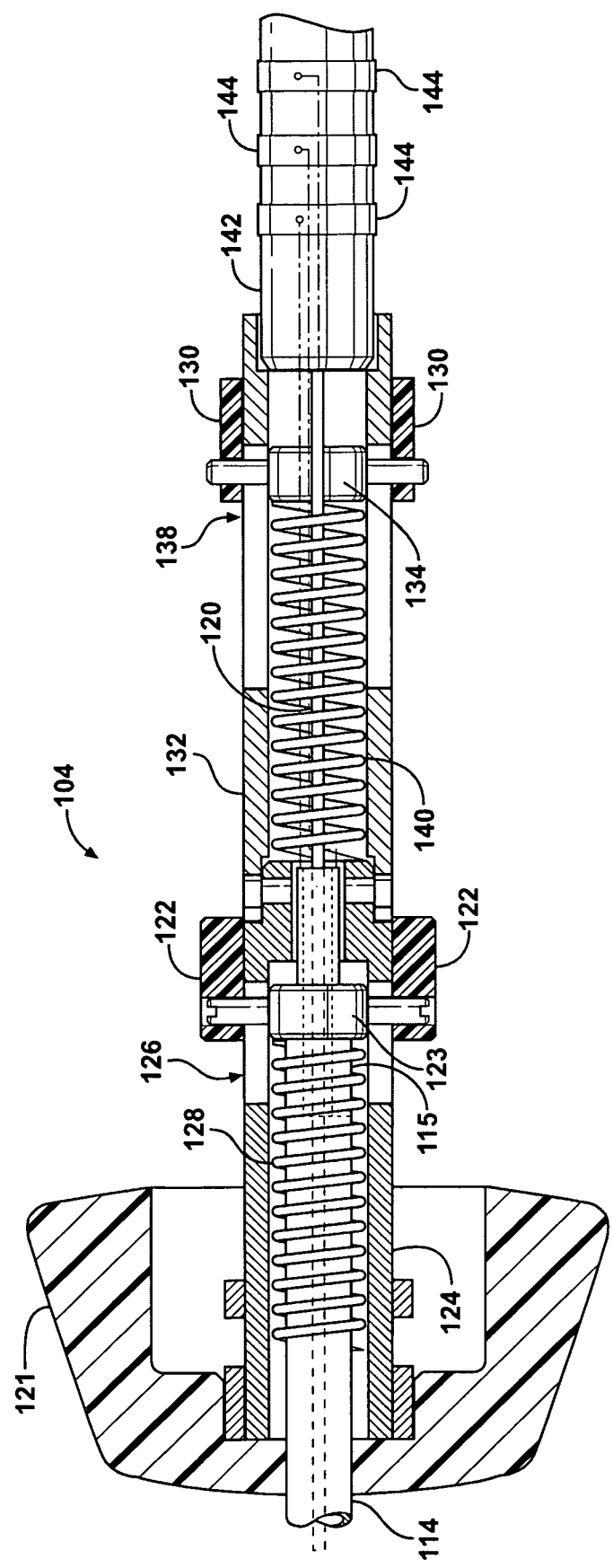
FIG. 14 is a partial cross-sectional view of the tool cartridge of the second embodiment showing an interior of first and second sheaths.
Figure 15:
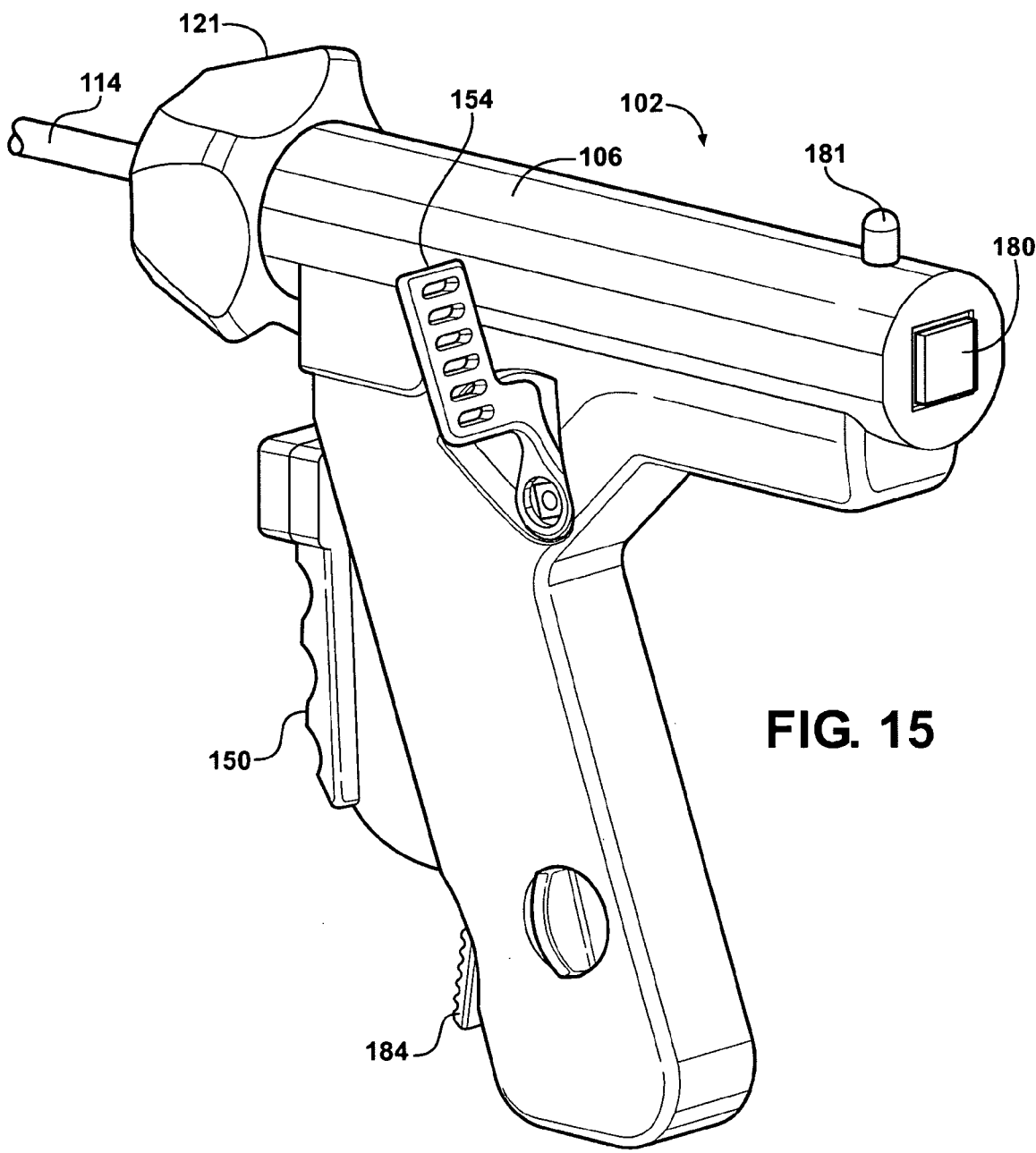
FIG. 15 is a perspective view of the handle assembly of the second embodiment showing a polarity switch.
Figure 20:
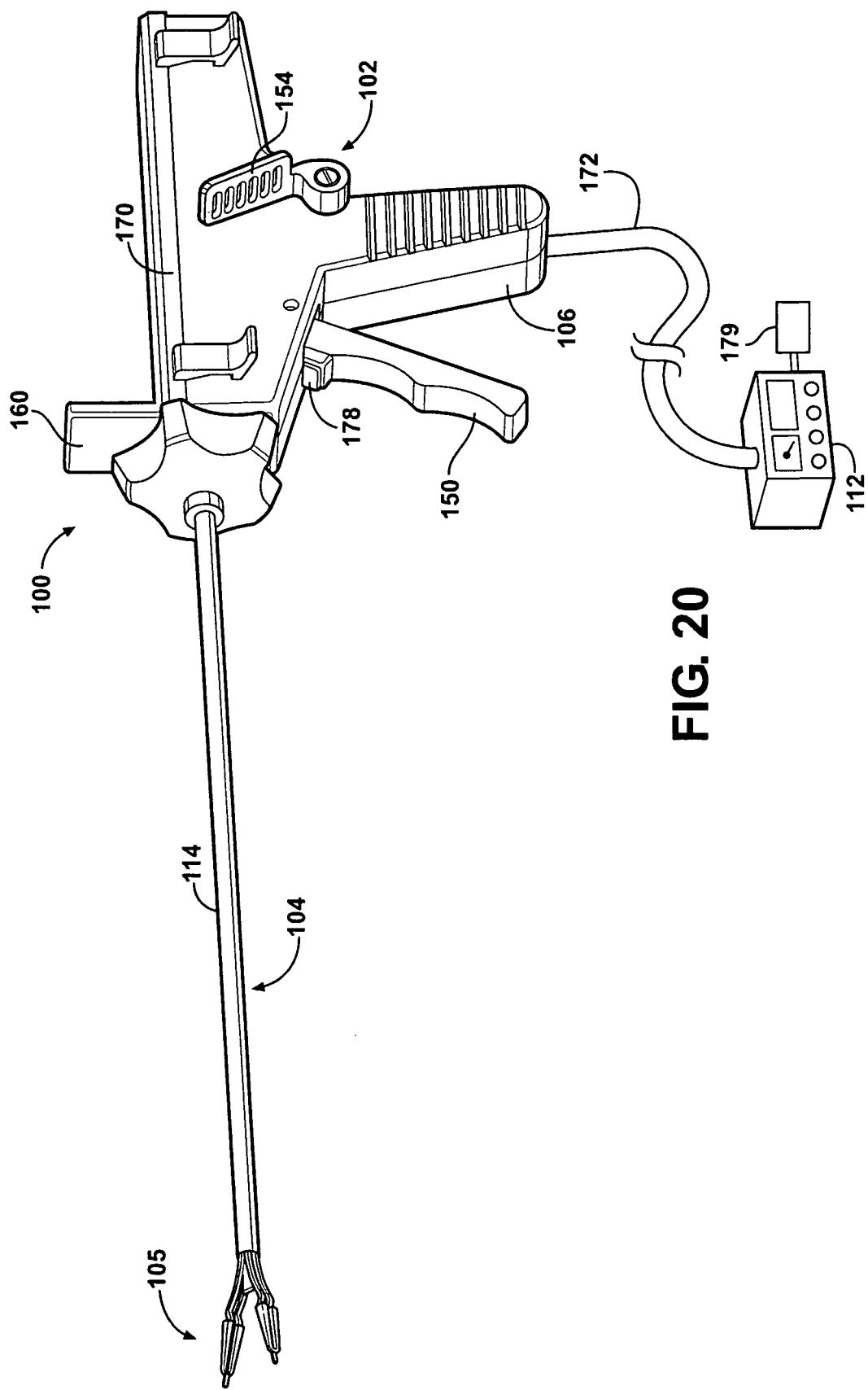
FIG. 20 is a perspective view of a third embodiment of the surgical apparatus showing the tool cartridge installed in the handle assembly.
Figure 21:
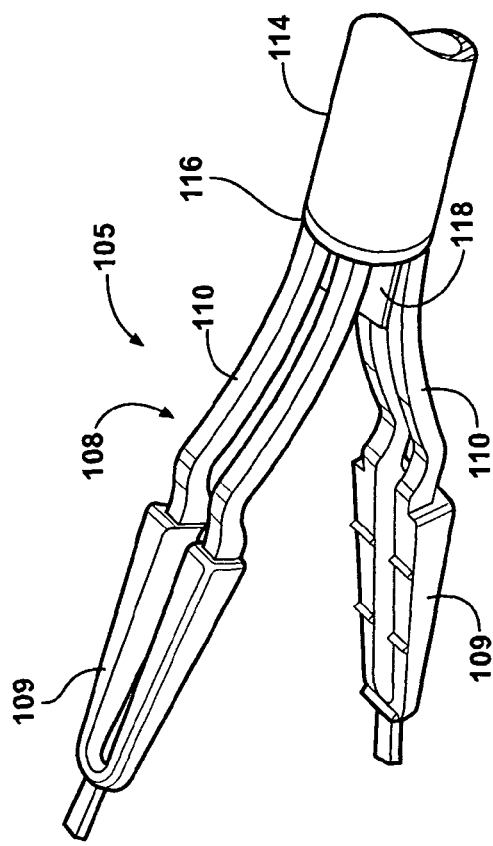
FIG. 21 is a close-up perspective view of the pair of jaws of the third embodiment.

Referring to FIGS. 1, 10, and 20, the surgical apparatus 100 includes a handle assembly 102 accommodating a tool cartridge 104. Three main embodiments for the surgical apparatus 100 are shown herein. Specifically, a first embodiment is shown in FIG. 1-9, a second embodiment is shown in FIGS. 10-19, and a third embodiment is shown in FIGS. 20-30.

In the first and third embodiments, the tool cartridge 104 is removable from the handle assembly 102 and replaceable. The tool cartridge 104 may be reusable, disposable, or reposable (i.e., used a limited number of times) while the handle assembly 102 may be used any number of times with different tool cartridges 104. The handle assembly 102 can accommodate a variety of different tool cartridges 104 where each tool cartridge 104 has specific scope and functionality. In the second embodiment, tool cartridge 104 is not removable from the handle assembly 102. That is, the handle assembly 102 and tool cartridge 104 are one unit that is typically disposed of after use. The tool cartridge 104 includes at least one tool 105 for use in a surgical procedure, preferably in an electrosurgical procedure. The handle assembly 102 may be held by a surgeon or other medical personnel, for operating the tool or tools 105 of the tool cartridge 104.

The handle assembly 102 includes a housing 106. The tool cartridge 104 is at least partially receivable in the housing 106 of the handle assembly 102. That is, the housing 106 supports the tool cartridge 104 by interfacing with at least part of the tool cartridge 104. The housing 106 of the handle assembly 102 defines an opening 107 for accommodating the tool cartridge 104 such that part of the tool cartridge 104 is disposed inside the housing 106 and part of the tool cartridge is disposed outside the housing 106.

In some implementations, such as those shown in FIGS. 1-5, 10-13, and 20-22, the tools 105 of the tool cartridge 104 includes a pair of jaws 108. The jaws 108 are movable with respect to one another for grasping the tissue T, as best shown in FIGS. 10 and 11. That is, the jaws 108 move toward one another to grasp the tissue T therebetween and move away from each other to release the tissue. Preferably, each jaw 108 includes a grasping portion 109 and a support portion 110. The grasping portion 109 may include a plurality of serrated teeth (not numbered). The support portion 110 supports the grasping portion 109. In the illustrated embodiments, the support portion 110 for each jaw includes a pair of rigid wires (not numbered) connected to the grasping portion 109.

The jaws 108 are each electrically connectable to a power source 112. Specifically, the jaws 108 are electrically connectable to the power source 112 when the tool cartridge 104 is properly installed in the handle assembly 102. As such, the jaws 108 may conduct electricity to the tissue T for use in surgical cutting and coagulating procedures. The power source 112 may be an electrosurgical generator, such as the Bovie ICON GP, manufactured by Bovie Medical Corporation located in St. Petersburg, Fla. However, alternative devices may be implemented as the power source 112. The power source 112 preferably generates an AC waveform in the radio frequency (RF) range. However, those skilled in the art realize other suitable electrical characteristics generated by the power source 112, including, but not limited to, DC power.

The tool cartridge 104 includes at least one transmission (not separately numbered) operatively connected to the tool 105 for operating the tool. In the illustrated implementations involving the jaws 108, the transmission is implemented as an extension tube 114 having a proximal end 115 and a distal end 116. The tube 114 is movable longitudinally, i.e., lengthwise, in a back-and-forth fashion. Movement of the tube 114 may be caused by the handle assembly 102, as described in more detail below.

The distal end 116 of the extension tube 114 operatively engages the jaws 108. More specifically, the tube 114 encompasses part of the support portions 110 of the jaws 108, such that the distal end 116 of the extension tube 114 engages the support portions 110 of the jaws 108. Movement of the extension tube 114 toward the grasping portions 109 results in the tube 114 encompassing more of the support portions 110. That is, the tube 114 compresses the support portions 110, resulting in movement of the grasping portions 109 with respect to one another.

The tools 105 of the tool cartridge 104 may also include at least one blade 118, as is shown in FIGS. 1-7, 10-13, and 20-22. The blade 118 is movable longitudinally to cut the tissue T. When implemented with the jaws 108, the blade 118 may be movable between the jaws 108 such that it is used to cut the tissue T that is grasped by the jaws 108. The transmission is implemented as a wire 120 which is operatively connected to the blade 118 for controlling movement of the blade 118, as will be described in detail below. Preferably, the wire 120 extends through the tube 114.

The blade 118 is electrically connectable to the power source 112 for conducting electricity to the tissue. More specifically, the wire 120 conducts electricity from the power source 112 to the blade 118. The blade 118 and jaws 108 may operate in a monopolar or bipolar fashion, as described in detail below.

The tools 105 of the tool cartridge 104 may also include one or more electrodes 190, as shown in FIGS. 6 and 7. In the illustrated implementations, the electrodes 190 extend through and are supported by the tube 114. The electrodes 190 are stationary, i.e., they do not open and close. The blade 118 may be disposed between the electrodes 190. A nonconductive coating 192 may be applied to the electrodes 190 adjacent the blade 118 to electrically isolate the electrodes 190 from the blade 118, thus directing electric current through the tissue T.

In the illustrated embodiments, the tool cartridge 104 includes a knob 121. The knob 121 surrounds the tube 114 and allows the surgeon to easily rotate the tool cartridge 104 when interfaced with the handle assembly 102.

The tool cartridge 104 includes one or more grips 122, 130 to facilitate movement of the tools 105. In some implementations, a first grip 122 is operatively connected to the extension tube 114 for facilitating movement of the tube 114 and thus movement of the jaws 108. The tool cartridge 104 also preferably includes a first sheath 124 encompassing at least part of the tube 114. The first sheath 124 is preferably tubular or cylindrically shaped and the first grip 122 is preferably ring shaped to encompass and slidably engage the first sheath 124. Other shapes and designs of the first grip 122 and first sheath 124 may be contemplated by those skilled in the art.

In some implementations, a first piston 123 disposed within the first sheath 124. Preferably, the first piston 123 is disc shaped to slidably engage with the tubular shaped first sheath 124. The first piston 123 is operatively connected to the tube 114, preferably by a direct connection. The first sheath 124 also defines at least one slot 126. In the illustrated embodiments, the first piston 123 and the first grip 122 are connected with two screws (not numbered) disposed through the slot 126. Of course, those skilled in the art realize other techniques to connect the first piston 123 and the first grip 122.

Preferably, the tool cartridge 104 also includes a first spring 128 disposed around the tube 114 and engagable with the first piston 123. The first spring 128 may also engage the knob 121. The first spring 128 provides tension against the first grip 122. The first sheath 124 preferably surrounds the first spring 128. As such, the first sheath 124 conceals and protects the first spring 128 from dirt and damage.

The tool cartridge 104 preferably includes a second grip 130 operatively connected to the wire 120 for facilitating movement of the blade 118. The tool cartridge 104 also preferably includes a second sheath 132 encompassing at least part of the wire 120. In the illustrated embodiments, the second sheath 132 is tubular or cylindrically shaped. The second sheath 132 is preferably connected to the first sheath 124 in an end-to-end manner.

In some implementations, a second piston 134 is disposed within the second sheath 132. The second piston 134 is preferably connected to the wire 120 and disc shaped to slidably engage the second sheath 132. The second grip 130 is preferably ring shaped and slidably engagable with the second sheath 132. The second sheath 132 also defines at least one slot 138. In the illustrated embodiments, the second piston 134 and the second grip 130 are connected with two screws (not numbered) disposed through the slot 138. Of course, those skilled in the art realize other techniques to connect the second piston 134 and the second sheath 132.

Preferably, the tool cartridge 104 also includes a second spring 140 engagable with the second piston 134. More specifically, the second spring 140 is disposed within the second sheath 132. The second spring 140 may also engage an end of the first sheath 124, which narrows for connection with the second sheath 132. As the second piston 134 and second grip 130 are connected, the second spring 140 provides tension against the second grip 130. The second spring 140 also encircles the wire 120 connected to the blade 118. Furthermore, the second sheath 132 conceals and protects the second spring 140 and the wire 120 from dirt and damage.

In the illustrated embodiments, the tool cartridge 104 also includes a third sheath 142. The third sheath 142 is preferably connected to either the first sheath 124 or the second sheath 132 in an end-to-end manner. A plurality of conductive rings 144 encircle an outer surface (not numbered) of the third sheath 142. These conductive rings 144 are formed of an electrically conductive material and utilized to interface electrical power between the handle assembly 102 and the tool cartridge 104. More specifically, the conductive rings 144 are electrically connected to the jaws 108, blade 118, and/or electrodes 190.

The handle assembly 102 includes a first tool actuation lever 150. The first tool actuation lever 150 is preferably pivotably hinged to allow motion about a pin (not numbered). The first tool actuation lever 150 is operatively engagable with the first grip 122 of the tool cartridge 104. Accordingly, in some embodiments, depression of the first tool actuation lever 150 moves the first grip 122 and the tube 114 to actuate the jaws 108 in relation to actuation of the first tool actuation lever 150.

Figure 25:
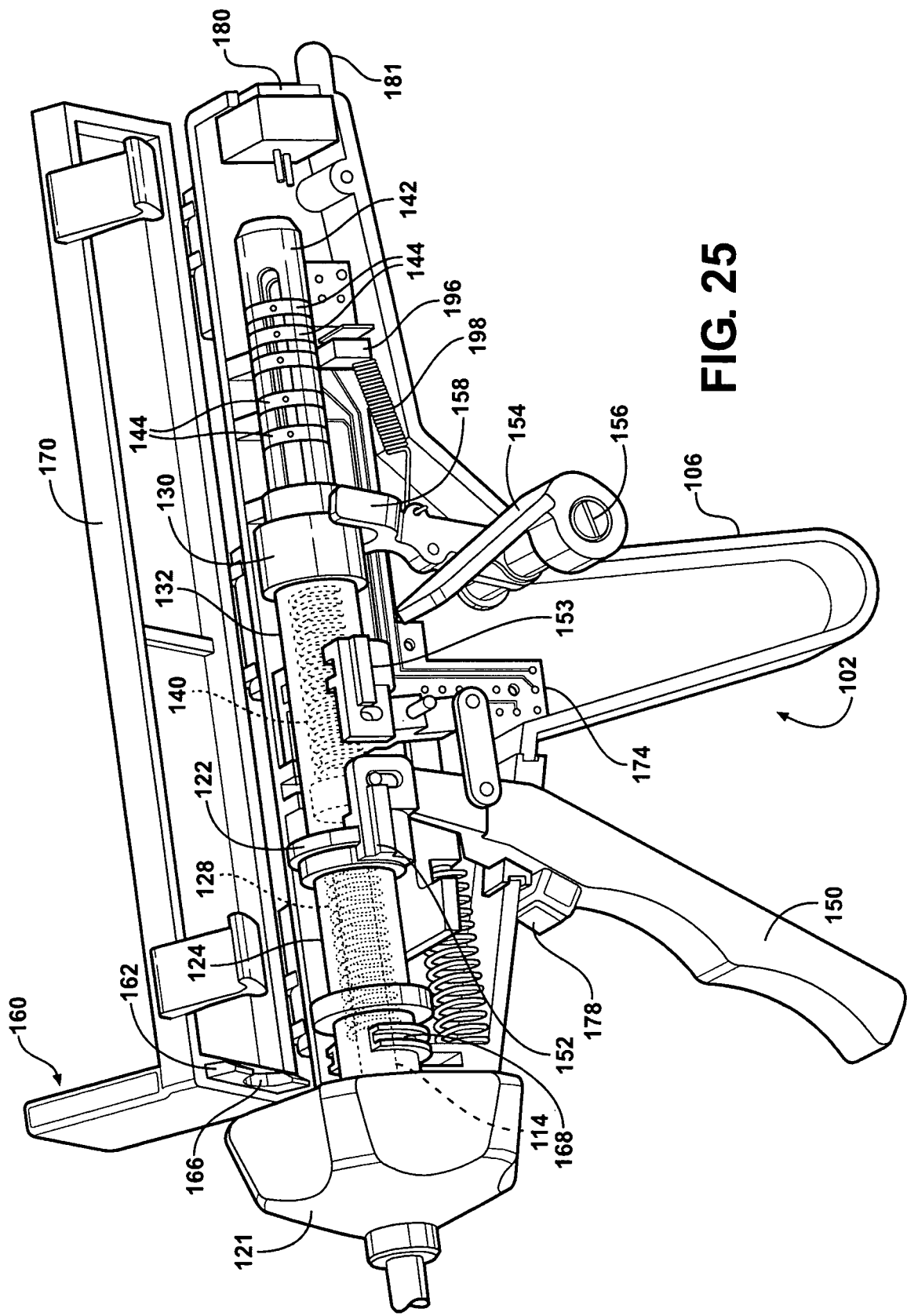
FIG. 25 is a perspective view of the third embodiment of the handle assembly with part of a housing removed and a lid opened and the tool cartridge installed therein.
Figure 26:
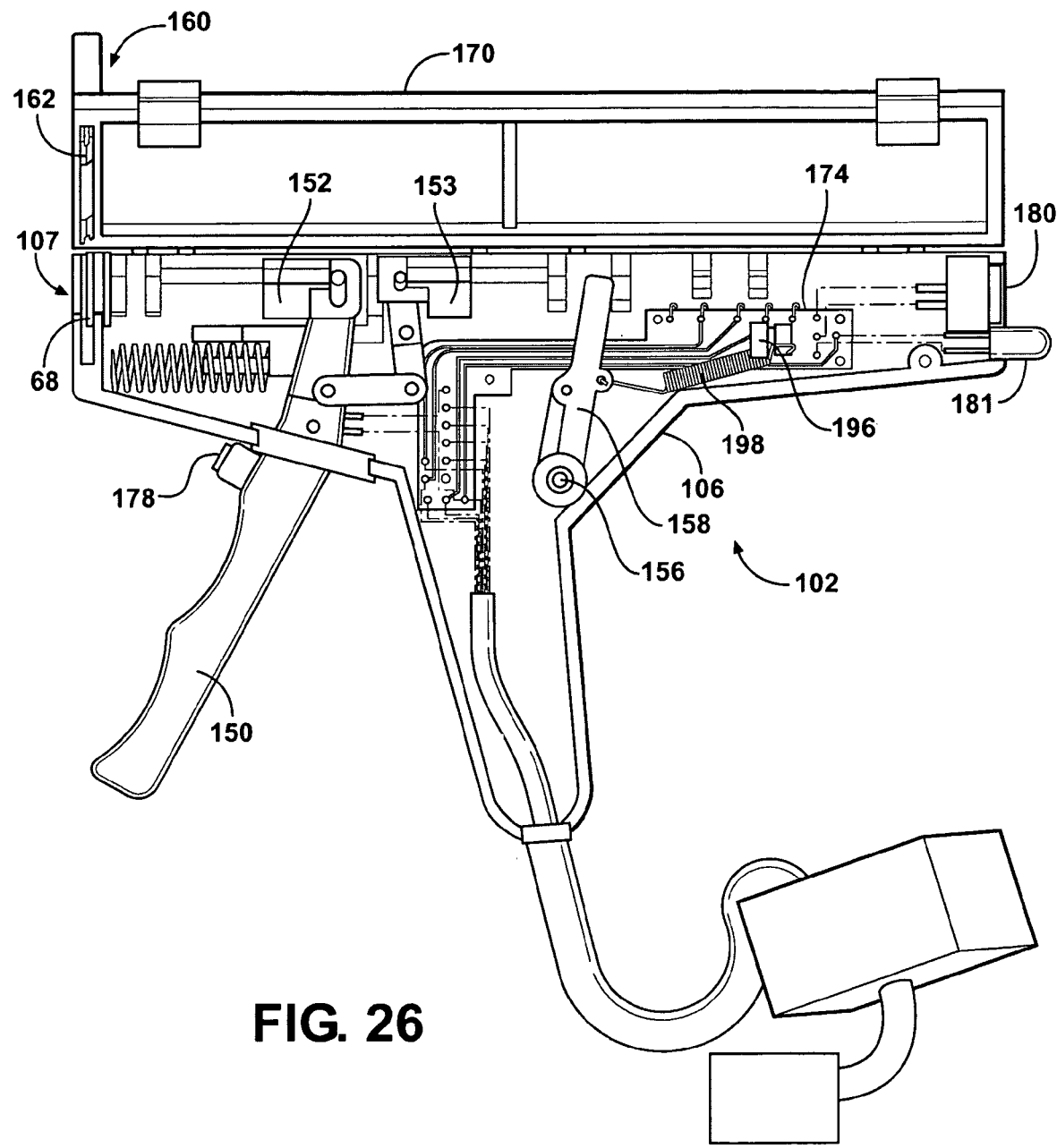
FIG. 26 is a side view of the third embodiment of the handle assembly with part of the housing removed and the lid opened.
Figure 27:
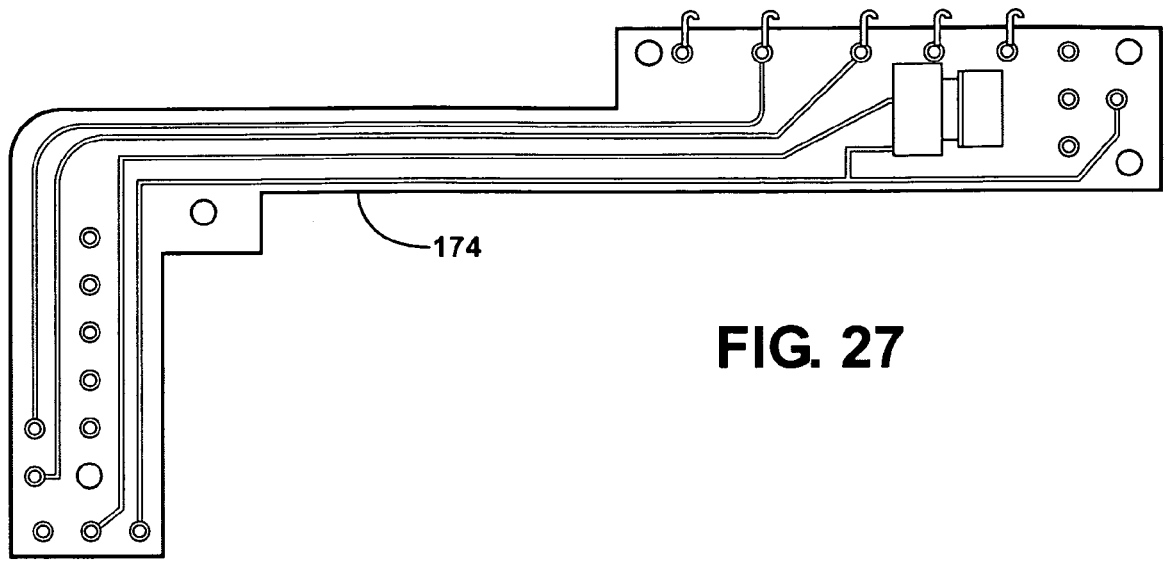
FIG. 27 is a front view of the PCB of the handle assembly of the third embodiment.
Figure 28:
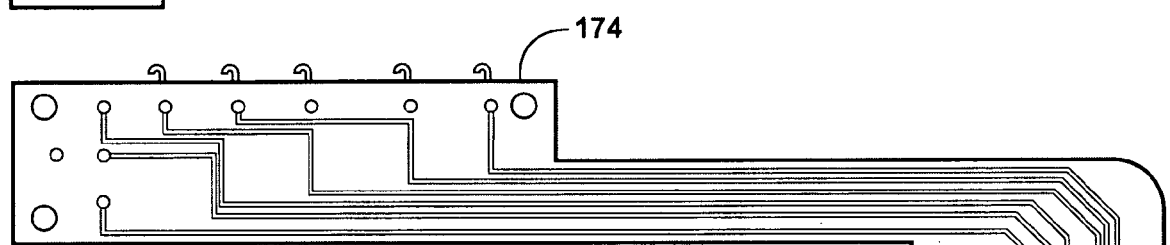
FIG. 28 is a back view of the PCB of the handle assembly of the third embodiment.
Figure 29:
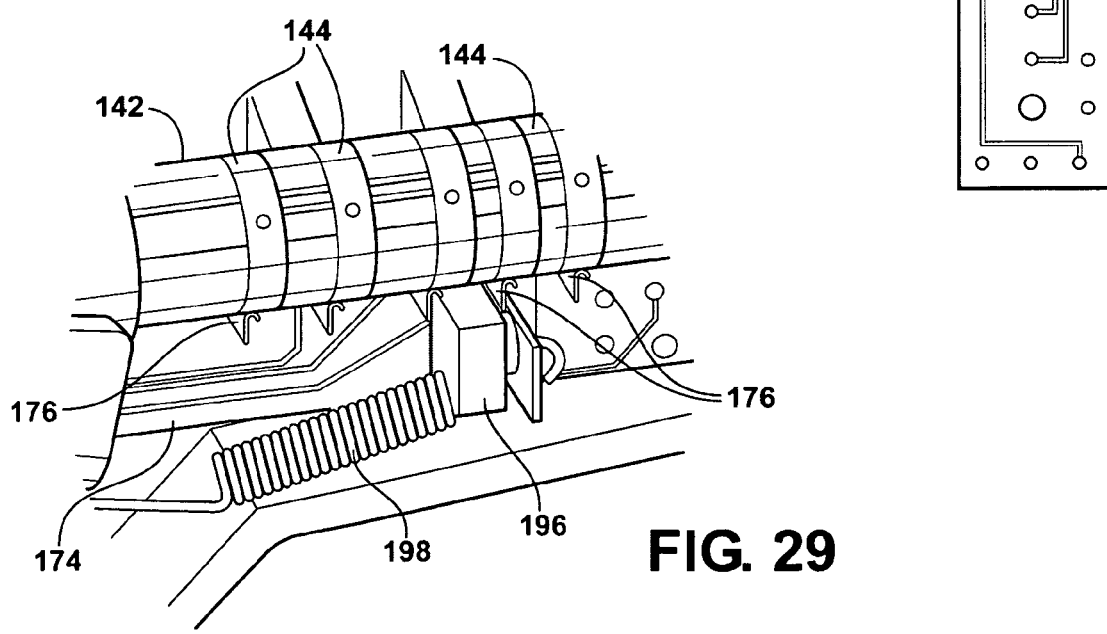
FIG. 29 is a close-up perspective view of electrical contacts of the third embodiment electrically connecting the PCB to conductive rings of the handle assembly.

The first tool actuation lever 150 is positioned both inside and outside of the housing 106 such that a user of the apparatus 100 may actuate the first tool actuation lever 150. Preferably, the first tool actuation lever 150 includes a first forked part 152 extending thereof. The first forked part 152 contacts the first grip 122. The third embodiment of the handle assembly 102 includes an auxiliary forked part 153 operatively connected to the first tool actuation lever 150, as shown in FIGS. 25 and 26. The auxiliary forked part 153 may actuate other grips (not numbered) on the tool assembly 104.

The handle assembly 102 also includes a second tool actuation lever 154. The second tool actuation lever 154 is preferably pivotably hinged to allow motion about a pin 156. In the illustrated embodiments, the second tool actuation lever 154 is operatively connected to the second grip 130 of the tool cartridge 104. Accordingly, depression of the second tool actuation lever 154 moves the second grip 130 and the wire 120 to actuate the blade 118 in relation to actuation of the second tool actuation lever 154.

The second tool actuation lever 154 is positioned outside of the housing 106 such that a user of the apparatus 100 may actuate the second tool actuation lever 154. A second forked part 158 is operatively connected to the pin 156. The second forked part 158 contacts the second grip 130 to effectuate movement of the second grip 130.

Importantly, the tool cartridge 104 of the illustrated embodiments may be rotated in a full 360° rotation while maintaining full mechanical and electrical operation. That is, no matter how much the tool cartridge 104 is rotated, the operation of the jaws 108 may be opened and closed, the blade 118 may be extended and retracted, and electrical current may flow to the jaws 108, the blade 118, and/or the electrodes 190. This functionality is a product of the ring shape of the grips 122, 130 working in conjunction with the fork parts 152, 153, 158 along with the conductive rings 144 contacting the electrical contacts 176.

Figure 30:
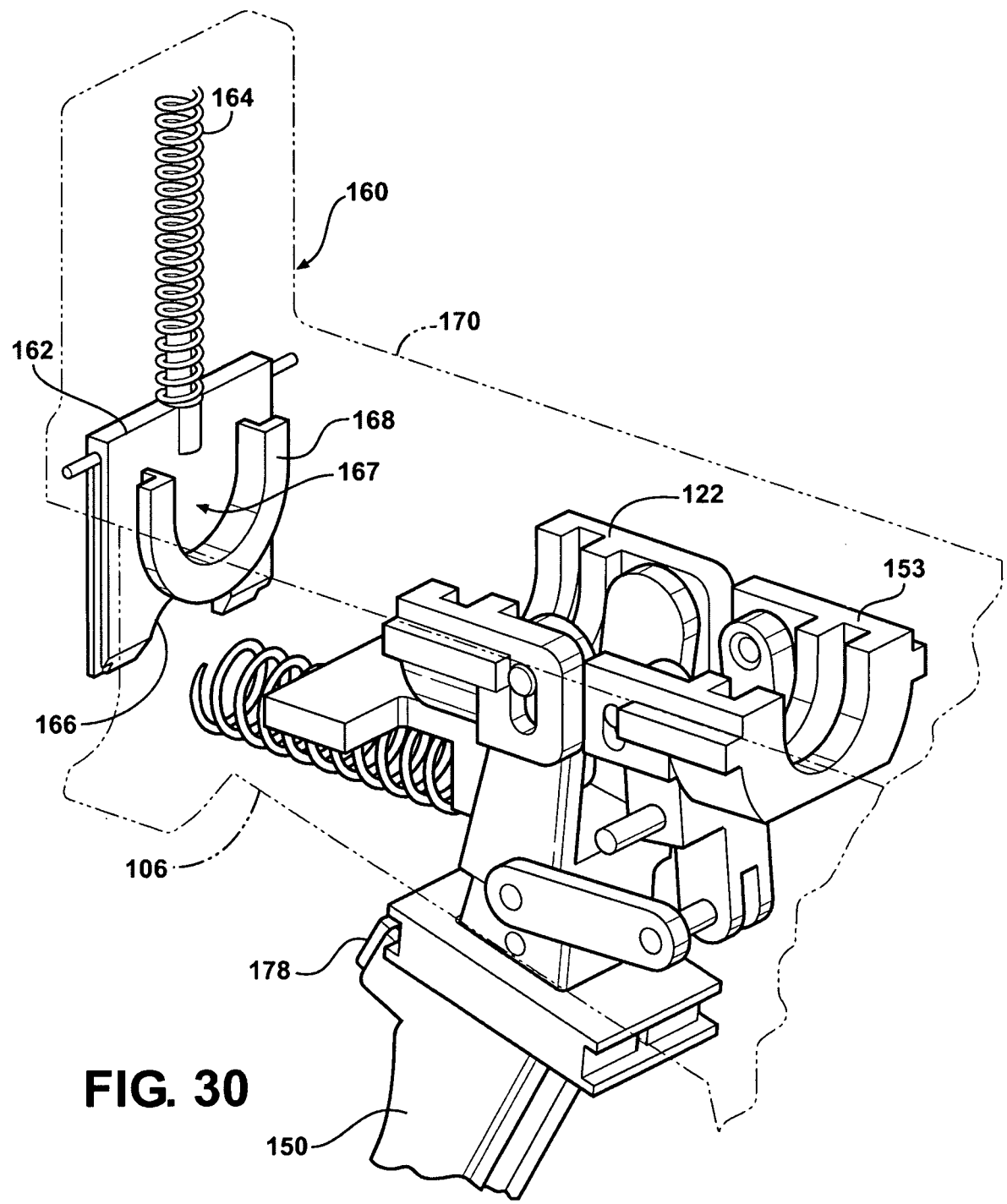
FIG. 30 is a perspective view of an interior of the housing of the third embodiment showing a gate mechanism for shuttering an opening of the housing.

The handle assembly 102 may also include a gate mechanism 160 for shuttering the opening 107 of the housing 106 when no tool cartridge 104 is interfaced with the handle assembly 102. The third embodiment of the handle assembly 102 includes such a gate mechanism 160, as shown in FIGS. 24-26 and 30. Referring primarily to FIG. 30, the gate mechanism 160 includes a gate 162 tensioned by a spring 164. The gate 162 includes a semi-circular edge 166 which engages the tool cartridge 104 when installed in the handle assembly 102. Furthermore, the gate 162 forces the tool cartridge 104 against a seal 168 disposed adjacent the opening 107.

The housing 106 of the third embodiment also includes a lid 170 that is openable for insertion and removal of the tool cartridge 104. The gate mechanism 160 is supported by the lid 170 such that the gate 162 is moved into engagement with the tool cartridge 104 when the lid 170 is closed.

The handle assembly 102 is electrically connectable to the power source 112 via a cable 172. The cable 172 preferably includes a plurality of conductors (not numbered) for conduction of electrical power and/or data between the handle assembly 102 and the power source 112.

The handle assembly 102 may include a printed circuit board (PCB) 174 disposed within the housing 106. In the second and third embodiments, the conductors of the cable 172 are electrically connected to the PCB 174. A plurality of electrical contacts 176 are electrically connected to and supported by the PCB 174. The electrical contacts 176 make contact with the conductive rings 144 of the tool cartridge 104.

The handle assembly 102 further includes a power switch 178 electrically connected to the PCB 174 for initiating conduction of electrical power from the power source 112 to the jaws 108 and/or blade 118. The power switch 178 is preferably a pushbutton and preferably disposed in close proximity to the first tool actuation lever 150. As such, the user of the apparatus 100 can easily initiate electrical power after closing the jaws 108 on the tissue. In the second and third embodiments, the power switch 178 is disposed within first tool actuation lever 150.

Figure 16:
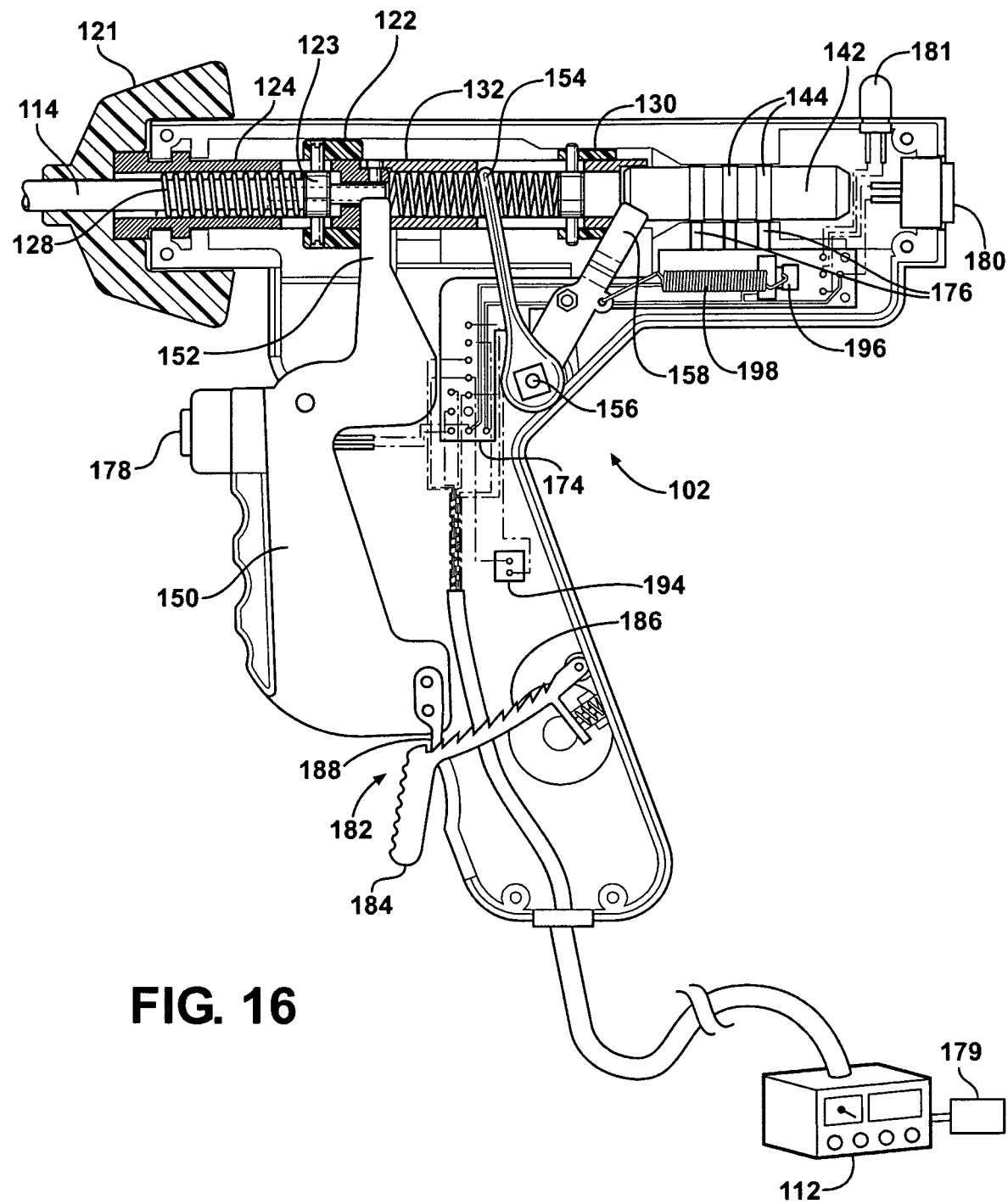
FIG. 16 is a partial cross-sectional view of the handle assembly of the second embodiment with the tool cartridge installed therein.
Figure 17:
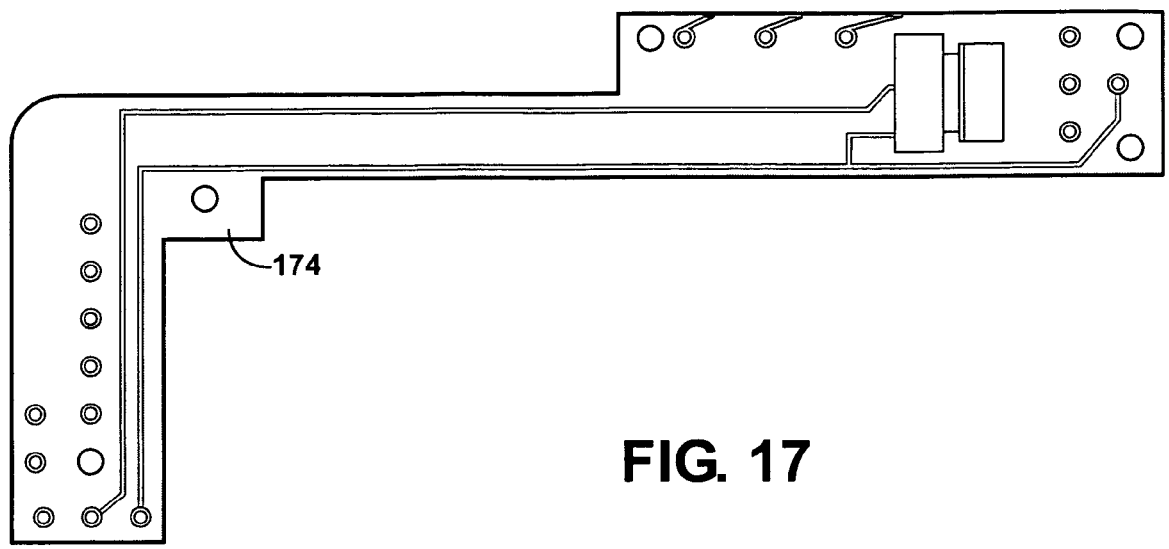
FIG. 17 is a front view of a printed circuit board (PCB) of the handle assembly of the second embodiment.
Figure 18:
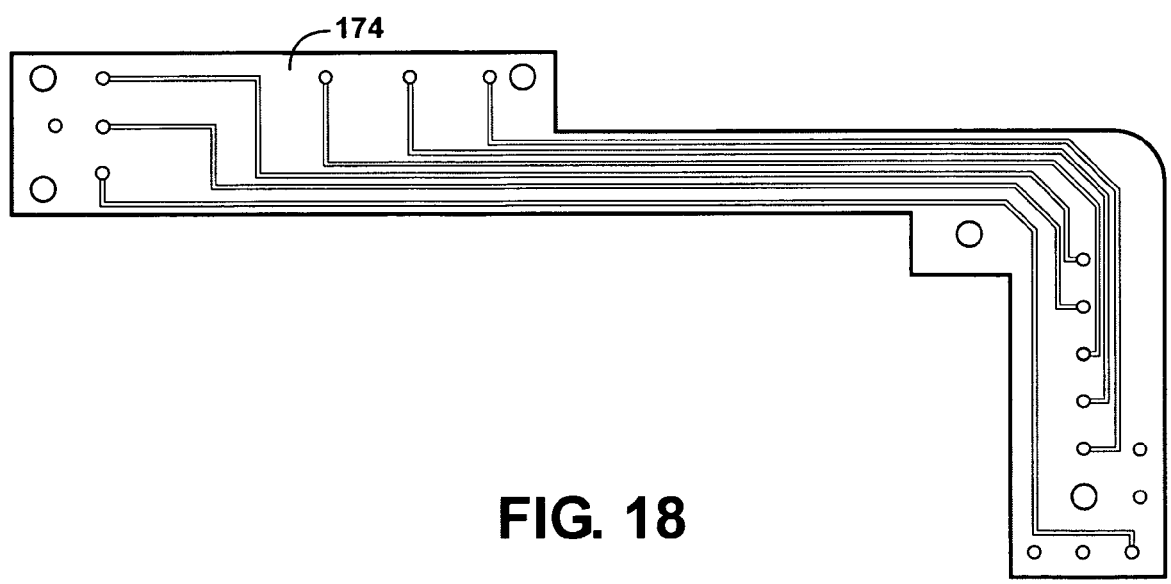
FIG. 18 is a back view of the PCB of the handle assembly of the second embodiment.
Figure 19:
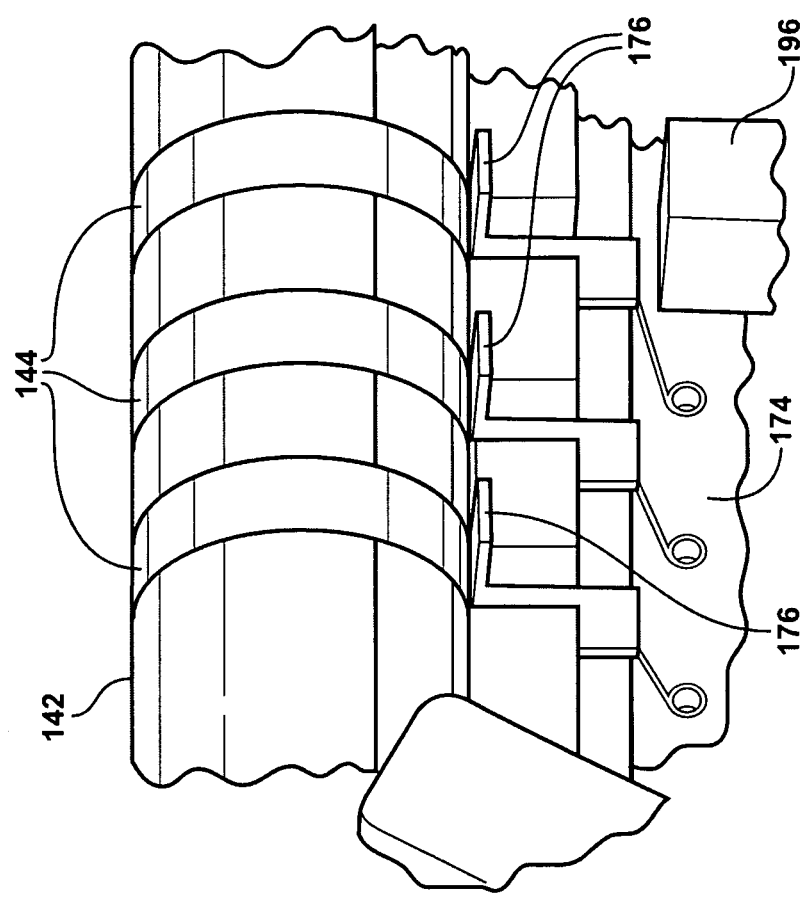
FIG. 19 is a close-up perspective view of electrical contacts of the second embodiment electrically connecting the PCB to conductive rings of the handle assembly.

The handle assembly 102 also preferably includes a cut-coag switch 196. The cut-coag switch 196 is preferably disposed within the housing and is operatively connected to the second forked part 158. Thus, the cut-coag switch 196 is operatively connected to the second tool actuation lever 154 as well. In the illustrated embodiments, such as is shown in FIG. 16, an extension spring 198 connects the cut-coag switch 196 to the second forked part 158. The cut-coag switch 196 is electrically connected to the PCB 174 for switching the apparatus 100 between a coagulating mode and a cutting mode, as described in detail below. As the cut-coag 196 switch is preferably disposed within the housing 106, it is not directly activated by a surgeon, but rather by operation of the second tool actuation lever 154.

In bipolar operation, the apparatus 100 includes a coagulation mode and a cutting mode. When operating on tissue T, the coagulation mode is typically performed first to coagulate the blood and tissue proteins. As such, the blade 118 is retracted. Accordingly, the cut-coag switch 196 is not activated, i.e., the switch 196 is open. Therefore, in the coagulation mode, i.e., when the cut-coag switch 196 is not activated, electric current flows from one of the jaws 108 (or one of the electrodes 190) to the other of the jaws 108 (or the other of the electrodes 190).

After performing coagulation of the tissue, the surgeon proceeds to cut the tissue T. Using the apparatus 100, the surgeon will advance the blade 118 using the second tool actuation lever 154 (which, in turn, operates the second forked part 158). As the second forked part 158 is moved forward, the extension spring 198 activates the cut-coag switch 196. This turns the apparatus 100 into cutting mode. As such, the electric current is then conducted from the blade 118, through the tissue T, to the jaws 108 (or the electrodes 190). This allows for superior cutting as both the sharp edge of the blade 118 and the electric current operate in tandem to cut the tissue T.

The electric waveform and cycle timing is typically different in the coagulation mode than in the cutting mode. For instance, in the coagulation mode, a pulsed RF waveform at a first frequency is typically used (e.g., 0.2 seconds on, and 0.8 seconds off). In the cutting mode, a constant RF waveform at a second frequency, different than the first frequency, is typically used. Those skilled in the art realize numerous techniques to produce suitable waveforms and cycle timing for the differing modes.

The handle assembly 102 may also include a polarity switch 180 electrically connected to the PCB 174. The polarity switch 180 allows selection of either monopolar or bipolar operation of the apparatus 100. Bipolar operation is described above with respect to either the coagulation mode or the cutting mode. In monopolar operation, electric current is conducted from the jaws 108 and the blade 118, through the tissue, to a conductive pad 179. Those skilled in the art realized that the conductive pad 179 is often referred to as a "ground pad". The conductive pad 179 is placed in contact with the body of the patient on whom the surgery is being performed such that a circuit is completed through the body of the patient.

By allowing convenient access to monopolar mode, the surgeon can easily switch the apparatus 100 from bipolar to monopolar (and back again if necessary) to complete the cutting operation. This on-the-fly switching is particularly useful for cutting "hard-to-cut" tissue T, which is often only realized during the middle of a coagulation and cutting procedure.

The handle assembly 102 may further include a light 181, such as a light emitting diode (LED). The light 181 is electrically connected to the PCB 174. In some embodiments, the light illuminates when the apparatus 100 is in monopolar operation.

The handle assembly 102 may also include a lever locking assembly 182. In the second embodiment, as best shown in FIG. 16, the lever locking assembly 182 is used to retain the first tool actuation lever 150 in position. The lever locking assembly 182 includes a plurality of teeth 186 in a saw-tooth configuration. The teeth 186 interface with a pin 188 extending from the first tool actuation lever 150. As the first tool actuation lever 150 is depressed, the pin 188 latches against one of the teeth 186. This holds the first tool actuation lever 150 (and accordingly the jaws 108) in position such that the surgeon need not retain pressure on the first tool actuation lever 150. The lever locking assembly also includes a tab 184 extending from the teeth 186 and positioned outside of the housing 106 to allow release of the pin 188 from the teeth.

Figure 23:
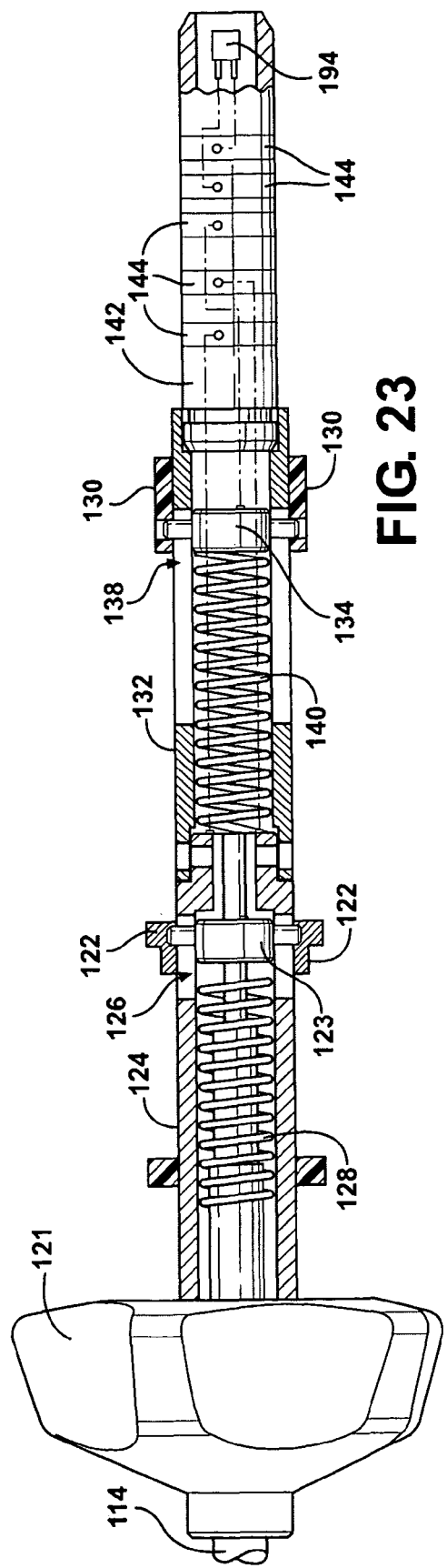
FIG. 23 is a partial cross-sectional view of the tool cartridge of the third embodiment showing the interior of the first and second sheaths.
Figure 22:
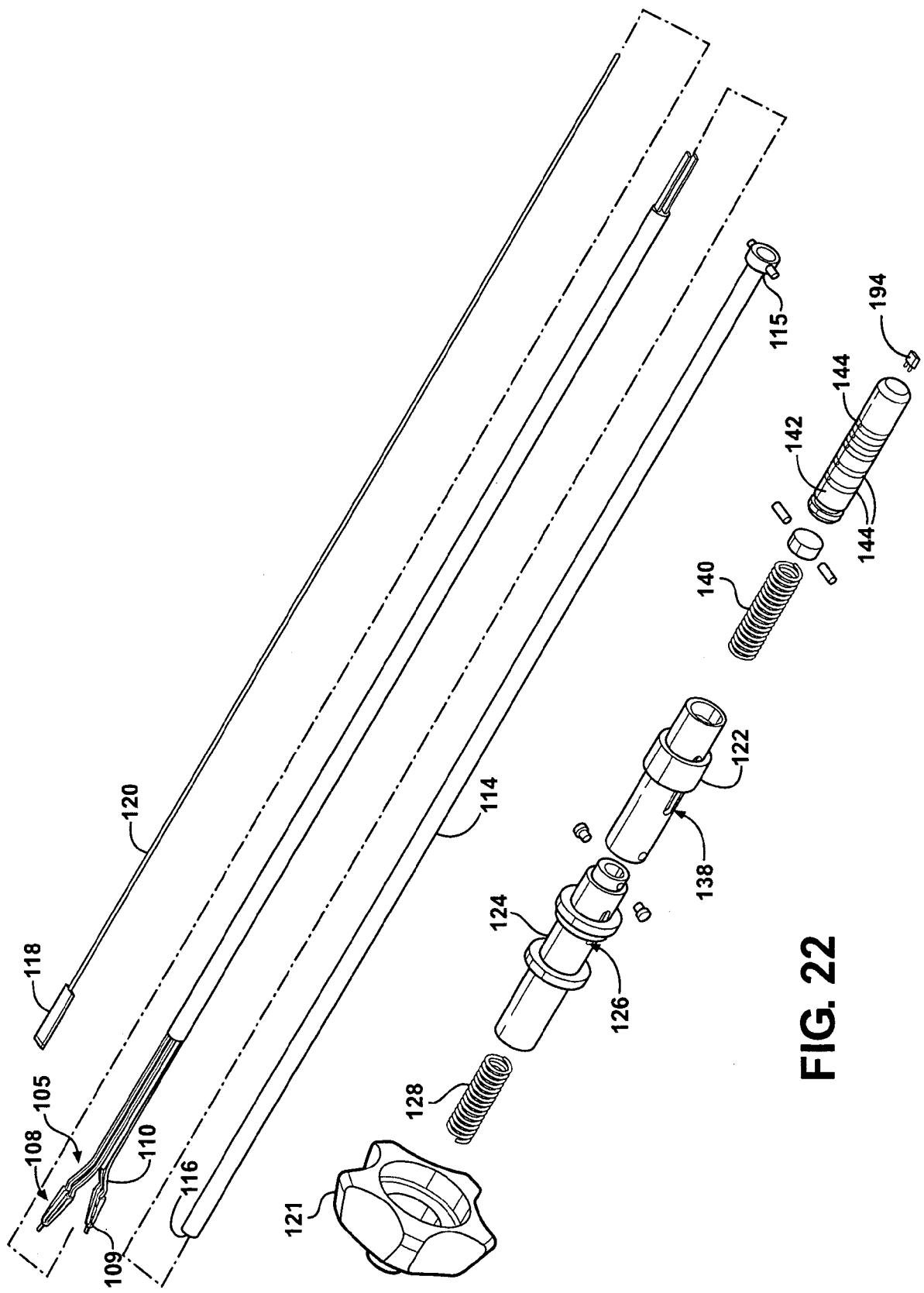
FIG. 22 is an exploded view of the tool cartridge of the third embodiment.
Figure 24:
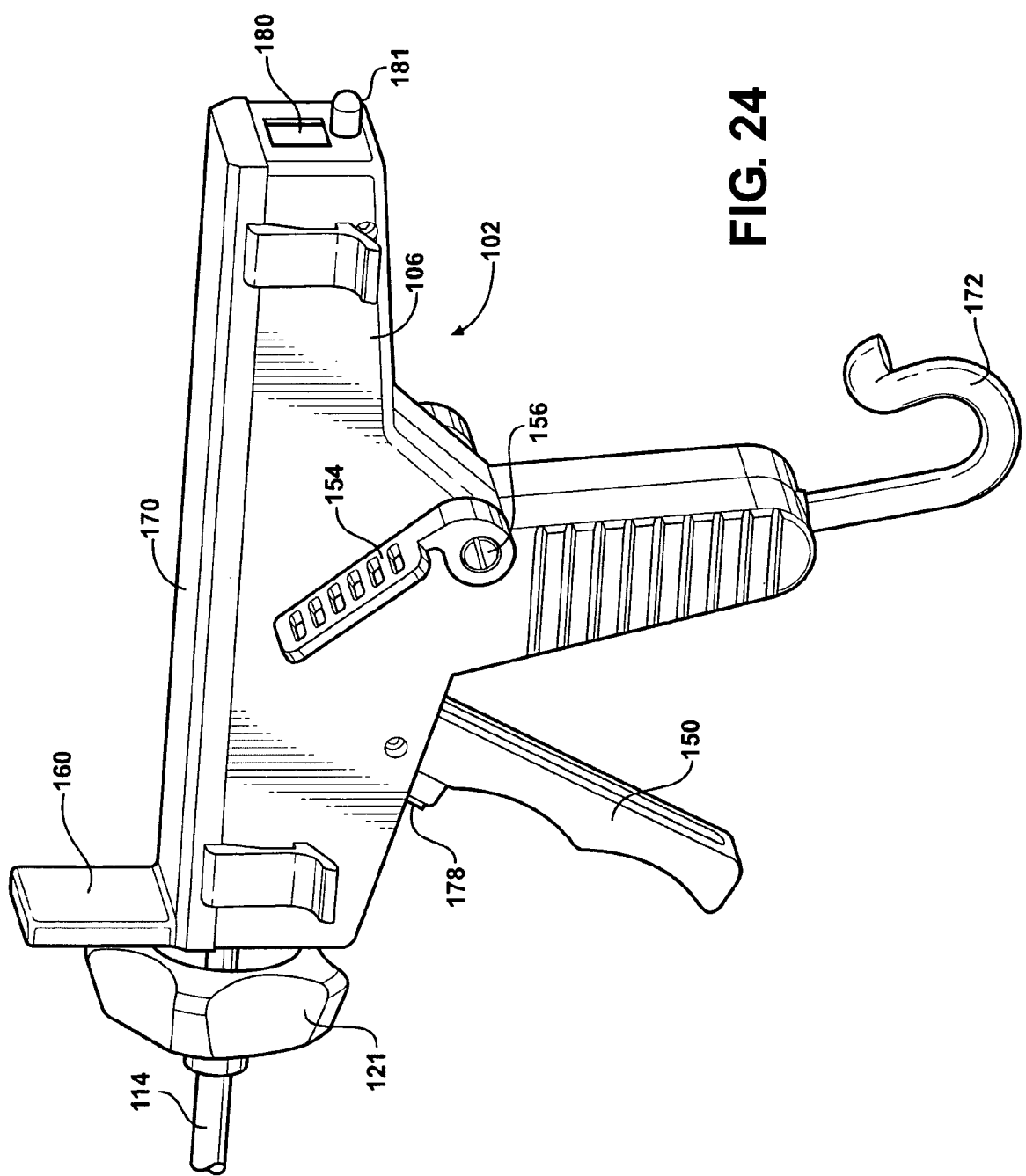
FIG. 24 is a perspective view of the third embodiment of the handle assembly.

The handle assembly 102 and/or the tool cartridge 104 may also include an identification chip 194. In the second embodiment, where the tool cartridge 104 is not removable from the handle assembly 102, the identification chip is preferably supported by the housing 106, as is shown in FIG. 16. In the third embodiment, where the tool cartridge 104 is replaceable, the identification chip 194 is preferably supported by the tool cartridge 104, as is shown in FIGS. 22 and 23. As the chip 194 is carried by the tool cartridge 104, electrical connections to the PCB 174 of the handle assembly 102 is accomplished via the conductive rings 114 and the electrical contacts 176.

The chip 194 contains identification data to identify the particular tool cartridge 104 that is installed in the housing 106. Particularly, the identification data may include a serial number, the particular tools 105 that the cartridge 104 carries, or other relevant information. The identification chip 194 is electrically connectable to the handle assembly via one or more of the contacts 176 and the PCB 174. Thus, the data stored on the identification chip 194 may be conveyed to the power source 172. The power source 172 may track the serial numbers provided by the identification chip 194 to limit the number of uses of each particular tool cartridge 104. The power source 172 may also launch an initial default setup to accommodate the characteristics of the specific tool cartridge 104 and/or apparatus 100.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. A surgical apparatus for coagulating and cutting tissue, said apparatus comprising:
    a handle assembly including a housing and at least one electrical contact;
    a tool cartridge at least partially receivable in said housing of said handle assembly and removable from said handle assembly;
    said tool cartridge including
        a tool for use in cutting tissue, the tool positioned at a distal end of the tool cartridge;
        a transmission operatively connected to said tool and longitudinally movable between positions;
        a first sheath positioned at a proximal end of the tool cartridge;
        at least one conductive ring encircling an outer surface of the first sheath;
        a second sheath enclosing at least part of said transmission and defining at least one slot, and
        a grip disposed outside of said second sheath and operatively connected to said transmission through said at least one slot; and
    said handle assembly including a tool actuation lever operatively engagable to said grip of said tool cartridge such that said grip and said transmission move to actuate said tool in relation to actuation of said tool actuation lever, wherein said at least one electrical contact engages said at least one conductive ring when the proximal end of said tool cartridge is received within said housing.

2. A surgical apparatus as set forth in claim 1 wherein said tool cartridge further includes a spring disposed within said second sheath and operatively connected to said grip for providing tension against said grip.

3. A surgical apparatus as set forth in claim 1 wherein said grip is ring shaped and surrounds and slidably engages said second sheath.

4. A surgical apparatus as set forth in claim 3 wherein said tool cartridge further includes a piston slidable within said second sheath and operatively connected to said transmission and said grip.

5. A surgical apparatus as set forth in claim 4 wherein said tool is electrically connectable to a power source for conducting electricity to the tissue.

6. A surgical apparatus as set forth in claim 5 wherein said tool cartridge is fully rotatable while maintaining mechanical control of said tool and electrical connection between said tool and said power source at any position of rotation.

7. A tool cartridge as set forth in claim 1 wherein said tool is further defined as a pair of jaws for grasping tissue, said transmission is further defined as an extension tube having a proximal end and a distal end, and said distal end of said extension tube operatively engages said jaws such that movement of said extension tube actuates movement of said jaws with respect to one another.

8. A surgical apparatus as set forth in claim 7 wherein said tool is further defined as a blade and said transmission is further defined as a wire operatively connected to said blade and extending through said extension tube.

9. A surgical apparatus as set forth in claim 1 wherein said tool is further defined as a pair of jaws and a blade, said transmission is further defined as an extension tube operatively engaging said jaws and a wire operatively connected to said blade, said second sheath further defined as a first sheath section enclosing part of said tube and a second sheath section enclosing part of said wire, said grip further defined as a first grip operatively connected to said tube and a second grip operatively connected to said wire, and a tool activation lever further defined as a first tool activation lever operatively engagable with said first grip and a second tool activation lever operatively engagable with said second grip.

10. A surgical apparatus as set forth in claim 9 wherein said second sheath section is connected to said first sheath section.

11. A surgical apparatus as set forth in claim 9 wherein said handle assembly includes a second tool actuation lever engagable with said second grip such that said second grip and said wire move to actuate said blade in relation to actuation of said second tool actuation lever.

12. A surgical apparatus as set forth in claim 1 wherein said housing of said handle assembly defines an opening for accommodating said tool cartridge such that part of said tool cartridge is disposed inside said housing and part of said tool cartridge is disposed outside said housing.

13. A surgical apparatus as set forth in claim 12 wherein said handle assembly includes a gate mechanism for shuttering said opening when no tool cartridge is interfaced with said handle assembly.

14. A surgical apparatus as set forth in claim 1 wherein said tool cartridge is reposable and/or disposable.

15. A surgical apparatus for coagulating and cutting tissue of a body, said apparatus comprising:
    a handle assembly having a first lever and a second lever, a housing, and at least one electrical contact;
    a tool cartridge at least partially receivable in said housing of said handle assembly and supported by said handle assembly;
    said tool cartridge including
        a pair of jaws positioned at a distal end of the tool cartridge, the pair of jaws electrically connected to a power source and movable in conjunction with said first lever for grasping the tissue,
        a sheath positioned at a proximal end of the tool cartridge,
        at least one conductive ring encircling an outer surface of the sheath, and
        a blade electrically connected to the power source and movable in conjunction with said second lever between longitudinal positions;
    said handle assembly also includes a cut-coag switch operatively connected to said second lever for automatically switching between a coagulation mode and a cutting mode as said blade is moved between positions, wherein said at least one electrical contact engages said at least one conductive ring when the proximal end of said tool cartridge is received within said housing.

16. An apparatus as set forth in claim 15 wherein electric current is conducted from one of said jaws, through the tissue, to the other of said jaws in said coagulation mode, and is conducted from said blade, through the tissue, to both of said jaws, in said cutting mode.

17. An apparatus as set forth in claim 16 further comprising a conductive pad positionable on the body and electrically connected to the power source and a switch supported by said handle assembly for switching between a monopolar mode and one of the bipolar coagulation mode and the bipolar cutting mode, wherein electric current is conducted from said jaws and said blade, through said tissue, and to said conductive pad in said monopolar mode.

* * * * *